(12) United States Patent
Imfeld et al.

(10) Patent No.: US 7,964,630 B2
(45) Date of Patent: Jun. 21, 2011

(54) TOPICAL APPLICATION AGENTS AGAINST MIMIC AND AGE-RELATED WRINKLES

(75) Inventors: Dominic Imfeld, Muenchenstein (CH); Hugo Ziegler, Witterswil (CH); Peter Wikstroem, Gipf-Oberfrick (CH)

(73) Assignee: DSM IP Assets B.V., Heerlen (NL)

( * ) Notice: Subject to any disclaimer, the term of this patent is extended or adjusted under 35 U.S.C. 154(b) by 376 days.

(21) Appl. No.: 11/718,496

(22) PCT Filed: Nov. 1, 2005

(86) PCT No.: PCT/CH2005/000638
§ 371 (c)(1), (2), (4) Date: Oct. 29, 2007

(87) PCT Pub. No.: WO2006/047900
PCT Pub. Date: May 11, 2006

(65) Prior Publication Data
US 2009/0111731 A1 Apr. 30, 2009

(30) Foreign Application Priority Data
Nov. 2, 2004 (CH) ..................... 1809/04

(51) Int. Cl.
*A61K 31/40* (2006.01)
*C07D 207/16* (2006.01)
(52) U.S. Cl. ...................... 514/423; 548/537
(58) Field of Classification Search .............. 514/2, 423, 514/326; 548/537; 546/208; 544/372; 530/330, 530/331
See application file for complete search history.

(56) References Cited

U.S. PATENT DOCUMENTS

| | | | |
|---|---|---|---|
| 3,966,701 A * | 6/1976 | Dorman et al. | 530/331 |
| 4,563,305 A * | 1/1986 | Ryan et al. | 530/331 |
| 6,169,074 B1 | 1/2001 | Montal et al. | |
| 7,408,027 B1 * | 8/2008 | Mandelkow et al. | 530/328 |

FOREIGN PATENT DOCUMENTS

EP 1 180 524 2/2002

OTHER PUBLICATIONS

Ito et al., In vitro non-thrombogenicity of a thrombin-substrate-immobilized polymer surface by the inhibition of thrombin activity, 1991, J. Biomater. Sci. Polymer Edn, vol. 2, No. 2, pp. 123-138.*
Hirase et al., N-Terminal tripeptide analogs of fibrin alpha-chain and their inhibitory effects on fibrinogen/thrombin clotting, 1989, Peptide Chemistry, Volume Date 1988, 26th, pp. 31-34.*

* cited by examiner

*Primary Examiner* — Kamal Saeed
*Assistant Examiner* — Kristin Bianchi
(74) *Attorney, Agent, or Firm* — Gottlieb, Rackman & Reisman PC

(57) ABSTRACT

The compounds of formula (I)

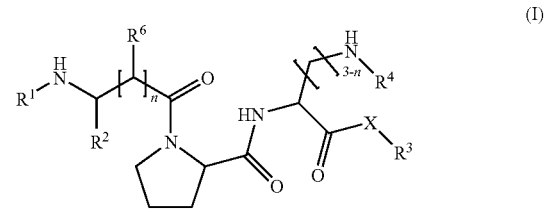

wherein
X represents a bond or NH—CH(C=O)—$(CH_2)_{3+n}$—NH—$R^5$,
n represents 0, 1 or 2,
$R^1$, $R^4$ and $R^5$—independently from each other—represent hydrogen, possibly substituted $C_1$-$C_6$-alkyl, amidino or tetra-$C_1$-$C_6$-alkylamidinium,
$R^2$ represents hydrogen or possibly substituted $C_1$-$C_6$-alkyl or $R^1$ and $R^2$ together with the residue to which they are bound represent a 5- to 7-membered, saturated ring,
$R^3$ represents $C_1$-$C_{12}$-alkoxy, $C_1$-$C_{12}$-alkylamino, possibly substituted aryl-$C_1$-$C_6$-alkylamino, possibly substituted heteroaryl-$C_1$-$C_6$-alkylamino, possibly substituted aryl-$C_1$-$C_6$-alkoxy or possibly substituted heteroaryl-$C_1$-$C_6$-alkoxy, and
$R^6$ represents hydrogen or, when n is 1, also amino or together with $R^1$ and the residue to which $R^6$ and $R^1$ are bound a 5- to 7-membered, saturated ring, as well as their physiologically acceptable salts are new. They can be manufactured according to common methods and processed to topically applicable compositions that are appropriate for treating mimic and age-related wrinkles in human skin.

34 Claims, No Drawings

TOPICAL APPLICATION AGENTS AGAINST MIMIC AND AGE-RELATED WRINKLES

Wrinkles mostly result from a strong muscular contraction or from a prolonged time in this position, respectively.

Today such mimic and age-related wrinkles are often treated with Botox (Botulinum toxin A). Botox is injected in the muscles which are thereby paralyzed. The muscles at the eyes or at the forehead don't operate any more, making the apparition of a forehead wrinkle impossible. However, the fact that the treatment with subcutaneously injected Botox has to be conducted by a doctor, its consequently high cost and its extremely high toxicity constitute considerable disadvantages of Botox. Its effectiveness lasts from 3 to 6 months, whereupon the treatment has to be repeated.

The mechanism of action of Botox consists in selectively blocking the acetylcholine release at the neuromuscular synapsis, leading to muscle paralysis. This occurs through splitting of a protein, the so-called SNAP-25.

The N-terminal amino acid sequence of SNAP-25 (H-Glu-Glu-Met-Gln-Arg-Arg-$NH_2$) also inhibits the $Ca^{++}$-dependent neurotransmitter release in the synapses and leads to muscle relaxation (EP1 180 524). The therefrom developed, topically applicable compound Ac-Glu-Glu-Met-Gln-Arg-Arg-$NH_2$ ("Product A") acts 5000 times weaker than Botox, can thus be dosed more easily and is hardly toxic. However, its muscle-relaxing effect is too weak and too inconstant to allow a satisfying wrinkle-reducing effect. A further disadvantage is its insufficient proteolytic stability.

Besides the Botox-inhibited release of the neurotransmitter acetylcholine, there are two further types of inhibitors of acetylcholine activity at the neuromuscular synapsis: inhibitors of the acetylcholine receptor (e.g. antihistamine, atropine) and of the acetylcholine esterase (e.g. insecticidal organophosphates).

Aim of the present invention was to find muscle-relaxing compounds to be applied as topical actives against mimic and age-related wrinkles, the action of which bases on the inhibition of the acetylcholine receptor and which don't present the disadvantages of Botox and of product A.

Surprisingly, we succeeded in finding new tripeptides, tripeptide-like compounds and derivatives thereof (hereinafter referred to as "compounds of the present invention") and topically applicable compositions for the treatment of mimic and age-related wrinkles that reach their site of action, the neuromuscular synapsis, rapidly and in sufficient concentration, block the latter and thereby induce a muscle-relaxing effect.

It could be shown that the compounds of the present invention have a clearly better activity profile with regard to muscle relaxation and a higher proteolytic stability than product A. Thanks to their relatively low molecular weight and to an appropriate water/n-octanol partition coefficient log P, they can be applied topically.

The present invention relates to tripeptides, tripeptide-like compounds and derivatives thereof of the general formula (I)

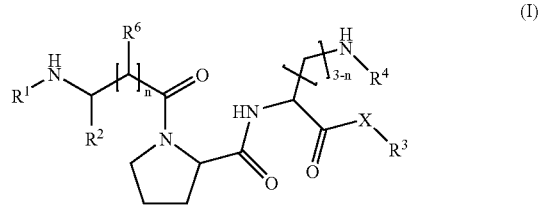

(I)

wherein

X represents a bond or NH—CH(C=O)—$(CH_2)_{3+n}$—NH—$R^5$, n represents 0, 1 or 2, $R^1$, $R^4$ and $R^5$—independently from each other—represent hydrogen, possibly substituted $C_1$-$C_6$-alkyl, amidino or tetra-$C_1$-$C_6$-alkylamidinium, $R^2$ represents hydrogen or possibly substituted $C_1$-$C_6$-alkyl, or $R^1$ and $R^2$ together with the residue to which they are bound represent a 5- to 7-membered, saturated ring, $R^3$ represents $C_1$-$C_{12}$-alkoxy, $C_1$-$C_{12}$-alkylamino, possibly substituted aryl-$C_1$-$C_6$-alkylamino, possibly substituted heteroaryl-$C_1$-$C_6$-alkylamino, possibly substituted aryl-$C_1$-$C_6$-alkoxy or possibly substituted heteroaryl-$C_1$-$C_6$-alkoxy and $R^6$ represents hydrogen or, when n is 1, also amino or together with $R^1$ and the residue to which $R^6$ and $R^1$ are bound a 5- to 7-membered, saturated ring, as racemates or pure enantiomers, as well as the salts thereof.

The present invention further relates to the use of the previously defined compounds and salts as topically applicable actives or for the preparation of topically applicable products, respectively, as well as topically applicable preparations containing at least one of the previously defined compounds or a salt thereof.

The above used general terms are defined as follows: "alkyl" as a group in itself and as a structural element of alkyl-containing groups means linear as well as branched, saturated hydrocarbon residues. Examples are methyl, ethyl, propyl, n-butyl, n-pentyl, n-hexyl, n-heptyl, n-octyl, n-nonyl, n-undecanyl, n-dodecanyl, n-tridecanyl, n-hexadecanyl, n-hepta-decanyl, n-octadecanyl and n-nonadecanyl as unbranched residues and isopropyl, tert.butyl, isobutyl, sec.butyl and isoamyl as branched ones.

"Aryl" refers to aromatic hydrocarbon residues, such as phenyl and naphthyl, phenyl being preferred.

"Heteroaryl" designates 5- to 11-membered, aromatic ring systems composed of one or two rings, in which 1 to 3 members are heteroatoms selected among oxygen, sulphur and nitrogen; 1 to 2 benzene rings may be condensed at the heterocycle. Examples are pyridyl, pyrimidinyl, pyridazinyl, pyrazinyl, 1,3,5-triazinyl, quinolinyl, isoquinolinyl, quinoxalinyl, quinazolinyl, phthalazinyl, pyrrolyl, pyrazolinyl, imidazolinyl, 1,2,4-triazolinyl, tetrazolinyl, furyl, thienyl, oxazolinyl, thiazolinyl, isothiazolinyl, benzoxazolyl, benzothienyl, indolyl, benzimidazolyl, indazolyl, benzotriazolyl and benzothiazolyl, whereby the connection can occur either to the hetero moiety or to the benzo moiety and for the π-excessive heteroaromatics over nitrogen or any carbon.

Examples for the 5- to 7-membered, saturated ring, that $R^1$ and $R^2$ or $R^1$ and $R^6$, respectively, may form together with the residue to which they are bound, are pyrrolidinyl, piperidinyl, piperazinyl, morpholinyl, azepinyl, oxazolidinyl, thiazolidinyl and 1,2,3,4-tetrahydroquinolinyl.

Substituents of the possibly substituted alkyl residues and of the groups containing these residues are, e.g., halogen, amino, guanidino, hydroxy, $C_1$-$C_6$-alkoxy, $C_1$-$C_6$-alkylthio, carboxy, carbamoyl, possibly substituted phenyl, possibly substituted benzyl, imidazolylmethyl, indolylmethyl and cyano.

Substituents of the possibly substituted aryl and heteroaryl groups are, e.g., halogen, $C_1$-$C_6$-alkyl, hydroxy, $C_1$-$C_6$-alkoxy, $C_1$-$C_6$-alkoxycarbonyl, CN, amino, $C_1$-$C_6$-alkylamino, di-$C_1$-$C_6$-alkylamino, aminocarbonyl, $C_1$-$C_6$-alkylaminocarbonyl, di-$C_1$-$C_6$-alkylaminocarbonyl, $C_1$-$C_6$-alkylthio, $C_1$-$C_6$-alkylsulfoxyl, $C_1$-$C_6$-alkylsulfonyl, possibly substituted benzyl, possibly substituted phenyl, possibly substituted phenoxy or possibly substituted phenylcarbonyl, whereby the above mentioned aromatic rings may be substituted with 1 to 3 identical or different substituents selected from the group comprising halogen, cyano, $C_1$-$C_6$-alkyl, $C_1$-$C_6$-alkoxy, hydroxy, amino, $C_1$-$C_6$-alkylamino, di-$C_1$-$C_6$-alkylamino and $C_1$-$C_6$-alkoxycarbonyl.

"Halogen" means fluorine, chlorine, bromine and iodine, fluorine and chlorine being preferred.

In formula I $R^1$ preferably represents hydrogen, $R^2$ preferably represents hydrogen or methyl, $R^3$ preferably represents aryl-$C_1$-$C_6$-alkylamino and n preferably represents 0 or 1. Particularly preferred are compounds of formula I, wherein $R^1$ means hydrogen, $R^2$ means hydrogen or methyl, $R^3$ means aryl-$C_1$-$C_6$-alkylamino and n means 0 or 1.

Particularly preferred compounds of the present invention are

H-Ala-Pro-Arg-Arg-NH-benzyl;
H-(β-Ala)-Pro-Dab-NH-benzyl;
H-Dap-Pro-Arg-NH-benzyl;
H-Ala-Pro-Arg-NH—(CH$_2$)$_2$-phenyl;
H-(β-Ala)-Pro-Gab-NH-benzyl;
N-[bis(dimethylamino)methylen]-Ala-Pro-Arg-NH-benzyl;

and acid addition salts of these compounds.

The different compounds in the following tables 1 to 3 illustrate the present invention.

TABLE 1

Compounds of formula (I), wherein X means a bond

| No. | $R^1$ | $R^2$ | $R^3$ | $R^4$ | n | $R^5$ |
|---|---|---|---|---|---|---|
| 1 | H | H | OCH$_3$ | H | 0 | — |
| 2 | H | H | OBenzyl | H | 0 | — |
| 3 | H | H | O(CH$_2$)$_2$Phenyl | H | 0 | — |
| 4 | H | H | O-3,5-F$_2$-Benzyl | H | 0 | — |
| 5 | H | H | OCH$_2$-2-Pyridyl | H | 0 | — |
| 6 | H | H | NH(CH$_2$)$_5$CH$_3$ | H | 0 | — |
| 7 | H | H | NHBenzyl | H | 0 | — |
| 8 | H | H | NH(CH$_2$)$_2$Phenyl | H | 0 | — |
| 9 | H | H | NH-3,5-F$_2$-Benzyl | H | 0 | — |
| 10 | H | H | NHCH$_2$-3-Pyridyl | H | 0 | — |
| 11 | H | CH$_3$ | OCH$_3$ | H | 0 | — |
| 12 | H | CH$_3$ | OBenzyl | H | 0 | — |
| 13 | H | CH$_3$ | O(CH$_2$)$_2$Phenyl | H | 0 | — |
| 14 | H | CH$_3$ | O-3,5-F$_2$-Benzyl | H | 0 | — |
| 15 | H | CH$_3$ | OCH$_2$-2-Pyridyl | H | 0 | — |
| 16 | H | CH$_3$ | NH(CH$_2$)$_5$CH$_3$ | H | 0 | — |
| 17 | H | CH$_3$ | NHBenzyl | H | 0 | — |
| 18 | H | CH$_3$ | NH(CH$_2$)$_2$Phenyl | H | 0 | — |
| 19 | H | CH$_3$ | NH-4-Cl-Benzyl | H | 0 | — |
| 20 | H | CH$_3$ | NHCH$_2$-3-Pyridyl | H | 0 | — |
| 21 | H | CH$_2$OH | OCH$_3$ | H | 0 | — |
| 22 | H | CH$_2$OH | OBenzyl | H | 0 | — |
| 23 | H | CH$_2$OH | O(CH$_2$)$_2$Phenyl | H | 0 | — |
| 24 | H | CH$_2$OH | O-3,5-F$_2$-Benzyl | H | 0 | — |
| 25 | H | CH$_2$OH | OCH$_2$-2-Pyridyl | H | 0 | — |
| 26 | H | CH$_2$OH | NH(CH$_2$)$_5$CH$_3$ | H | 0 | — |
| 27 | H | CH$_2$OH | NHBenzyl | H | 0 | — |
| 28 | H | CH$_2$OH | NH(CH$_2$)$_2$Phenyl | H | 0 | — |
| 29 | H | CH$_2$OH | NH-4-Cl-Benzyl | H | 0 | — |
| 30 | H | CH$_2$OH | NHCH$_2$-3-Pyridyl | H | 0 | — |
| 31 | H | (CH$_2$)$_2$NH$_2$ | OCH$_3$ | H | 0 | — |
| 32 | H | (CH$_2$)$_2$NH$_2$ | OBenzyl | H | 0 | — |
| 33 | H | (CH$_2$)$_2$NH$_2$ | O(CH$_2$)$_2$Phenyl | H | 0 | — |
| 34 | H | (CH$_2$)$_2$NH$_2$ | O-3,5-F$_2$-Benzyl | H | 0 | — |
| 35 | H | (CH$_2$)$_2$NH$_2$ | OCH$_2$-2-Pyridyl | H | 0 | — |
| 36 | H | (CH$_2$)$_2$NH$_2$ | NH(CH$_2$)$_5$CH$_3$ | H | 0 | — |
| 37 | H | (CH$_2$)$_2$NH$_2$ | NHBenzyl | H | 0 | — |
| 38 | H | (CH$_2$)$_2$NH$_2$ | NH(CH$_2$)$_2$Phenyl | H | 0 | — |
| 39 | H | (CH$_2$)$_2$NH$_2$ | NH-4-Cl-Benzyl | H | 0 | — |
| 40 | H | (CH$_2$)$_2$NH$_2$ | NHCH$_2$-3-Pyridyl | H | 0 | — |
| 41 | H | (CH$_2$)$_3$NH$_2$ | OCH$_3$ | H | 0 | — |
| 42 | H | (CH$_2$)$_3$NH$_2$ | OBenzyl | H | 0 | — |
| 43 | H | (CH$_2$)$_3$NH$_2$ | O(CH$_2$)$_2$Phenyl | H | 0 | — |
| 44 | H | (CH$_2$)$_3$NH$_2$ | O-3,5-F$_2$-Benzyl | H | 0 | — |
| 45 | H | (CH$_2$)$_3$NH$_2$ | OCH$_2$-2-Pyridyl | H | 0 | — |
| 46 | H | (CH$_2$)$_3$NH$_2$ | NH(CH$_2$)$_5$CH$_3$ | H | 0 | — |
| 47 | H | (CH$_2$)$_3$NH$_2$ | NHBenzyl | H | 0 | — |
| 48 | H | (CH$_2$)$_3$NH$_2$ | NH(CH$_2$)$_2$Phenyl | H | 0 | — |
| 49 | H | (CH$_2$)$_3$NH$_2$ | NH-4-Cl-Benzyl | H | 0 | — |
| 50 | H | (CH$_2$)$_3$NH$_2$ | NHCH$_2$-3-Pyridyl | H | 0 | — |
| 51 | H | CH$_2$NH$_2$ | NHBenzyl | H | 0 | — |
| 52 | H | (CH$_2$)$_4$NH$_2$ | NHBenzyl | H | 0 | — |
| 53 | H | (CH$_2$)$_3$NHC=NH(NH$_2$) | NHBenzyl | H | 0 | — |
| 54 | H | CH$_2$CH$_3$ | NHBenzyl | H | 0 | — |
| 55 | H | (CH$_2$)$_2$CH$_3$ | NHBenzyl | H | 0 | — |
| 56 | H | CH(CH$_3$)$_2$ | NHBenzyl | H | 0 | — |
| 57 | H | CH$_2$CH(CH$_3$)$_2$ | NHBenzyl | H | 0 | — |
| 58 | H | CH(CH$_3$)CH$_2$CH$_3$ | NHBenzyl | H | 0 | — |

TABLE 1-continued

Compounds of formula (I), wherein X means a bond

| No. | $R^1$ | $R^2$ | $R^3$ | $R^4$ | n | $R^5$ |
|---|---|---|---|---|---|---|
| 59 | H | $(CH_2)_2SCH_3$ | NHBenzyl | H | 0 | — |
| 60 | H | $CH_2COOH$ | NHBenzyl | H | 0 | — |
| 61 | H | $CH_2CONH_2$ | NHBenzyl | H | 0 | — |
| 62 | H | $(CH_2)_2OH$ | NHBenzyl | H | 0 | — |
| 63 | H | $CH(CH_3)OH$ | NHBenzyl | H | 0 | — |
| 64 | H | $(CH_2)_2COOH$ | NHBenzyl | H | 0 | — |
| 65 | H | $(CH_2)_2CONH_2$ | NHBenzyl | H | 0 | — |
| 66 | H | $CH_2Phenyl$ | NHBenzyl | H | 0 | — |
| 67 | H | $CH_2$-4-OH-Phenyl | NHBenzyl | H | 0 | — |
| 68 | H | Phenyl | NHBenzyl | H | 0 | — |
| 69 | H | $CH_2$-4-Imidazolyl | NHBenzyl | H | 0 | — |
| 70 | H | $CH_2$-3-Indolyl | NHBenzyl | H | 0 | — |
| 71 | H | H | NHBenzyl | Benzyl | 0 | — |
| 72 | H | $CH_3$ | NHBenzyl | Benzyl | 0 | — |
| 73 | H | $CH_2OH$ | NHBenzyl | Benzyl | 0 | — |
| 74 | H | $(CH_2)_2NH_2$ | NHBenzyl | Benzyl | 0 | — |
| 75 | H | $(CH_2)_3NH_2$ | NHBenzyl | Benzyl | 0 | — |
| 76 | H | $CH_2NH_2$ | NHBenzyl | Benzyl | 0 | — |
| 77 | H | $(CH_2)_4NH_2$ | NHBenzyl | Benzyl | 0 | — |
| 78 | H | $(CH_2)_3NHC=NH(NH_2)$ | NHBenzyl | Benzyl | 0 | — |
| 79 | H | $CH_2CH_3$ | NHBenzyl | Benzyl | 0 | — |
| 80 | H | $(CH_2)_2CH_3$ | NHBenzyl | Benzyl | 0 | — |
| 81 | H | $CH(CH_3)_2$ | NHBenzyl | Benzyl | 0 | — |
| 82 | H | $CH_2CH(CH_3)_2$ | NHBenzyl | Benzyl | 0 | — |
| 83 | H | $CH(CH_3)CH_2CH_3$ | NHBenzyl | Benzyl | 0 | — |
| 84 | H | $(CH_2)_2SCH_3$ | NHBenzyl | Benzyl | 0 | — |
| 85 | H | $CH_2COOH$ | NHBenzyl | Benzyl | 0 | — |
| 86 | H | $CH_2CONH_2$ | NHBenzyl | Benzyl | 0 | — |
| 87 | H | $(CH_2)_2OH$ | NHBenzyl | Benzyl | 0 | — |
| 88 | H | $CH(CH_3)OH$ | NHBenzyl | Benzyl | 0 | — |
| 89 | H | $(CH_2)_2COOH$ | NHBenzyl | Benzyl | 0 | — |
| 90 | H | $(CH_2)_2CONH_2$ | NHBenzyl | Benzyl | 0 | — |
| 91 | H | $CH_2Phenyl$ | NHBenzyl | Benzyl | 0 | — |
| 92 | H | $CH_2$-4-OH-Phenyl | NHBenzyl | Benzyl | 0 | — |
| 93 | H | Phenyl | NHBenzyl | Benzyl | 0 | — |
| 94 | H | $CH_2$-4-Imidazolyl | NHBenzyl | Benzyl | 0 | — |
| 95 | H | $CH_2$-3-Indolyl | NHBenzyl | Benzyl | 0 | — |
| 96 | H | H | NHBenzyl | $C=NH(NH_2)$ | 0 | — |
| 97 | H | $CH_3$ | NHBenzyl | $C=NH(NH_2)$ | 0 | — |
| 98 | H | $CH_2OH$ | NHBenzyl | $C=NH(NH_2)$ | 0 | — |
| 99 | H | $(CH_2)_2NH_2$ | NHBenzyl | $C=NH(NH_2)$ | 0 | — |
| 100 | H | $(CH_2)_3NH_2$ | NHBenzyl | $C=NH(NH_2)$ | 0 | — |
| 101 | H | $CH_2NH_2$ | NHBenzyl | $C=NH(NH_2)$ | 0 | — |
| 102 | H | $(CH_2)_4NH_2$ | NHBenzyl | $C=NH(NH_2)$ | 0 | — |
| 103 | H | $(CH_2)_3NHC=NH(NH_2)$ | NHBenzyl | $C=NH(NH_2)$ | 0 | — |
| 104 | H | $CH_2CH_3$ | NHBenzyl | $C=NH(NH_2)$ | 0 | — |
| 105 | H | $(CH_2)_2CH_3$ | NHBenzyl | $C=NH(NH_2)$ | 0 | — |
| 106 | H | $CH(CH_3)_2$ | NHBenzyl | $C=NH(NH_2)$ | 0 | — |
| 107 | H | $CH_2CH(CH_3)_2$ | NHBenzyl | $C=NH(NH_2)$ | 0 | — |
| 108 | H | $CH(CH_3)CH_2CH_3$ | NHBenzyl | $C=NH(NH_2)$ | 0 | — |
| 109 | H | $(CH_2)_2SCH_3$ | NHBenzyl | $C=NH(NH_2)$ | 0 | — |
| 110 | H | $CH_2COOH$ | NHBenzyl | $C=NH(NH_2)$ | 0 | — |
| 111 | H | $CH_2CONH_2$ | NHBenzyl | $C=NH(NH_2)$ | 0 | — |
| 112 | H | $(CH_2)_2OH$ | NHBenzyl | $C=NH(NH_2)$ | 0 | — |
| 113 | H | $CH(CH_3)OH$ | NHBenzyl | $C=NH(NH_2)$ | 0 | — |
| 114 | H | $(CH_2)_2COOH$ | NHBenzyl | $C=NH(NH_2)$ | 0 | — |
| 115 | H | $(CH_2)_2CONH_2$ | NHBenzyl | $C=NH(NH_2)$ | 0 | — |
| 116 | H | $CH_2Phenyl$ | NHBenzyl | $C=NH(NH_2)$ | 0 | — |
| 117 | H | $CH_2$-4-OH-Phenyl | NHBenzyl | $C=NH(NH_2)$ | 0 | — |
| 118 | H | Phenyl | NHBenzyl | $C=NH(NH_2)$ | 0 | — |
| 119 | H | $CH_2$-4-Imidazolyl | NHBenzyl | $C=NH(NH_2)$ | 0 | — |
| 120 | H | $CH_2$-3-Indolyl | NHBenzyl | $C=NH(NH_2)$ | 0 | — |
| 121 | H | H | NHBenzyl | H | 1 | H |
| 122 | H | $CH_3$ | NHBenzyl | H | 1 | H |
| 123 | H | $CH_2OH$ | NHBenzyl | H | 1 | H |
| 124 | H | $(CH_2)_2NH_2$ | NHBenzyl | H | 1 | H |
| 125 | H | $(CH_2)_3NH_2$ | NHBenzyl | H | 1 | H |
| 126 | H | $CH_2NH_2$ | NHBenzyl | H | 1 | H |
| 127 | H | $(CH_2)_4NH_2$ | NHBenzyl | H | 1 | H |
| 128 | H | $(CH_2)_3NHC=NH(NH_2)$ | NHBenzyl | H | 1 | H |
| 129 | H | $CH_2CH_3$ | NHBenzyl | H | 1 | H |
| 130 | H | $(CH_2)_2CH_3$ | NHBenzyl | H | 1 | H |
| 131 | H | $CH(CH_3)_2$ | NHBenzyl | H | 1 | H |
| 132 | H | $CH_2CH(CH_3)_2$ | NHBenzyl | H | 1 | H |
| 133 | H | $CH(CH_3)CH_2CH_3$ | NHBenzyl | H | 1 | H |
| 134 | H | $(CH_2)_2SCH_3$ | NHBenzyl | H | 1 | H |

TABLE 1-continued

Compounds of formula (I), wherein X means a bond

| No. | R¹ | R² | R³ | R⁴ | n | R⁵ |
|---|---|---|---|---|---|---|
| 135 | H | CH$_2$COOH | NHBenzyl | H | 1 | H |
| 136 | H | CH$_2$CONH$_2$ | NHBenzyl | H | 1 | H |
| 137 | H | (CH$_2$)$_2$OH | NHBenzyl | H | 1 | H |
| 138 | H | CH(CH$_3$)OH | NHBenzyl | H | 1 | H |
| 139 | H | (CH$_2$)$_2$COOH | NHBenzyl | H | 1 | H |
| 140 | H | (CH$_2$)$_2$CONH$_2$ | NHBenzyl | H | 1 | H |
| 141 | H | CH$_2$Phenyl | NHBenzyl | H | 1 | H |
| 142 | H | CH$_2$-4-OH-Phenyl | NHBenzyl | H | 1 | H |
| 143 | H | Phenyl | NHBenzyl | H | 1 | H |
| 144 | H | CH$_2$-4-Imidazolyl | NHBenzyl | H | 1 | H |
| 145 | H | CH$_2$-3-Indolyl | NHBenzyl | H | 1 | H |
| 146 | H | H | NHBenzyl | H | 2 | H |
| 147 | H | CH$_3$ | NHBenzyl | H | 2 | H |
| 148 | H | CH$_2$OH | NHBenzyl | H | 2 | H |
| 149 | H | (CH$_2$)$_2$NH$_2$ | NHBenzyl | H | 2 | H |
| 150 | H | (CH$_2$)$_3$NH$_2$ | NHBenzyl | H | 2 | H |
| 151 | H | CH$_2$NH$_2$ | NHBenzyl | H | 2 | H |
| 152 | H | (CH$_2$)$_4$NH$_2$ | NHBenzyl | H | 2 | H |
| 153 | H | (CH$_2$)$_3$NHC=NH(NH$_2$) | NHBenzyl | H | 2 | H |
| 154 | H | CH$_2$CH$_3$ | NHBenzyl | H | 2 | H |
| 155 | H | (CH$_2$)$_2$CH$_3$ | NHBenzyl | H | 2 | H |
| 156 | H | CH(CH$_3$)$_2$ | NHBenzyl | H | 2 | H |
| 157 | H | CH$_2$CH(CH$_3$)$_2$ | NHBenzyl | H | 2 | H |
| 158 | H | CH(CH$_3$)CH$_2$CH$_3$ | NHBenzyl | H | 2 | H |
| 159 | H | (CH$_2$)$_2$SCH$_3$ | NHBenzyl | H | 2 | H |
| 160 | H | CH$_2$COOH | NHBenzyl | H | 2 | H |
| 161 | H | CH$_2$CONH$_2$ | NHBenzyl | H | 2 | H |
| 162 | H | (CH$_2$)$_2$OH | NHBenzyl | H | 2 | H |
| 163 | H | CH(CH$_3$)OH | NHBenzyl | H | 2 | H |
| 164 | H | (CH$_2$)$_2$COOH | NHBenzyl | H | 2 | H |
| 165 | H | (CH$_2$)$_2$CONH$_2$ | NHBenzyl | H | 2 | H |
| 166 | H | CH$_2$Phenyl | NHBenzyl | H | 2 | H |
| 167 | H | CH$_2$-4-OH-Phenyl | NHBenzyl | H | 2 | H |
| 168 | H | Phenyl | NHBenzyl | H | 2 | H |
| 169 | H | CH$_2$-4-Imidazolyl | NHBenzyl | H | 2 | H |
| 170 | H | CH$_2$-3-Indolyl | NHBenzyl | H | 2 | H |
| 171 | C(CH$_3$)$_3$ | H | NHBenzyl | H | 1 | H |
| 172 | C(CH$_3$)$_3$ | CH$_3$ | NHBenzyl | H | 1 | H |
| 173 | C(CH$_3$)$_3$ | CH$_2$OH | NHBenzyl | H | 1 | H |
| 174 | C(CH$_3$)$_3$ | (CH$_2$)$_2$NH$_2$ | NHBenzyl | H | 1 | H |
| 175 | C(CH$_3$)$_3$ | (CH$_2$)$_3$NH$_2$ | NHBenzyl | H | 1 | H |
| 176 | C(CH$_3$)$_3$ | CH$_2$NH$_2$ | NHBenzyl | H | 1 | H |
| 177 | C(CH$_3$)$_3$ | (CH$_2$)$_4$NH$_2$ | NHBenzyl | H | 1 | H |
| 178 | C(CH$_3$)$_3$ | (CH$_2$)$_3$NHC=NH(NH$_2$) | NHBenzyl | H | 1 | H |
| 179 | C(CH$_3$)$_3$ | CH$_2$CH$_3$ | NHBenzyl | H | 1 | H |
| 180 | C(CH$_3$)$_3$ | (CH$_2$)$_2$CH$_3$ | NHBenzyl | H | 1 | H |
| 181 | C(CH$_3$)$_3$ | CH(CH$_3$)$_2$ | NHBenzyl | H | 1 | H |
| 182 | C(CH$_3$)$_3$ | CH$_2$CH(CH$_3$)$_2$ | NHBenzyl | H | 1 | H |
| 183 | C(CH$_3$)$_3$ | CH(CH$_3$)CH$_2$CH$_3$ | NHBenzyl | H | 1 | H |
| 184 | C(CH$_3$)$_3$ | (CH$_2$)$_2$SCH$_3$ | NHBenzyl | H | 1 | H |
| 185 | C(CH$_3$)$_3$ | CH$_2$COOH | NHBenzyl | H | 1 | H |
| 186 | C(CH$_3$)$_3$ | CH$_2$CONH$_2$ | NHBenzyl | H | 1 | H |
| 187 | C(CH$_3$)$_3$ | (CH$_2$)$_2$OH | NHBenzyl | H | 1 | H |
| 188 | C(CH$_3$)$_3$ | CH(CH$_3$)OH | NHBenzyl | H | 1 | H |
| 189 | C(CH$_3$)$_3$ | (CH$_2$)$_2$COOH | NHBenzyl | H | 1 | H |
| 190 | C(CH$_3$)$_3$ | (CH$_2$)$_2$CONH$_2$ | NHBenzyl | H | 1 | H |
| 191 | C(CH$_3$)$_3$ | CH$_2$Phenyl | NHBenzyl | H | 1 | H |
| 192 | C(CH$_3$)$_3$ | CH$_2$-4-OH-Phenyl | NHBenzyl | H | 1 | H |
| 193 | C(CH$_3$)$_3$ | Phenyl | NHBenzyl | H | 1 | H |
| 194 | C(CH$_3$)$_3$ | CH$_2$-4-Imidazolyl | NHBenzyl | H | 1 | H |
| 195 | C(CH$_3$)$_3$ | CH$_2$-3-Indolyl | NHBenzyl | H | 1 | H |
| 196 | —CH$_2$CH$_2$CH$_2$— | | NHBenzyl | H | 0 | — |
| 197 | —CH$_2$CH$_2$CH$_2$CH$_2$— | | NHBenzyl | H | 0 | — |
| 198 | —CH$_2$CH$_2$CH$_2$CH$_2$CH$_2$— | | NHBenzyl | H | 0 | — |
| 199 | —CH$_2$CH$_2$NHCH$_2$— | | NHBenzyl | H | 0 | — |
| 200 | —CH$_2$CH$_2$OCH$_2$— | | NHBenzyl | H | 0 | — |
| 201 | —CH$_2$SCH$_2$— | | NHBenzyl | H | 0 | — |
| 202 | —CH$_2$CH$_2$CH$_2$— | | NHBenzyl | H | 1 | H |
| 203 | —CH$_2$CH$_2$CH$_2$CH$_2$— | | NHBenzyl | H | 1 | H |
| 204 | —CH$_2$CH$_2$CH$_2$CH$_2$CH$_2$— | | NHBenzyl | H | 1 | H |
| 205 | —CH$_2$CH$_2$NHCH$_2$— | | NHBenzyl | H | 1 | H |
| 206 | —CH$_2$CH$_2$OCH$_2$— | | NHBenzyl | H | 1 | H |
| 207 | —CH$_2$SCH$_2$— | | NHBenzyl | H | 1 | H |
| 208 | —CH$_2$CH$_2$CH$_2$— | | NHBenzyl | C=NH(NH$_2$) | 0 | — |
| 209 | —CH$_2$CH$_2$CH$_2$CH$_2$— | | NHBenzyl | C=NH(NH$_2$) | 0 | — |
| 210 | —CH$_2$CH$_2$CH$_2$CH$_2$CH$_2$— | | NHBenzyl | C=NH(NH$_2$) | 0 | — |

TABLE 1-continued

Compounds of formula (I), wherein X means a bond

| No. | R¹ | R² | R³ | R⁴ | n | R⁵ |
|---|---|---|---|---|---|---|
| 211 | | —CH₂CH₂NHCH₂— | NHBenzyl | C=NH(NH₂) | 0 | — |
| 212 | | —CH₂CH₂OCH₂— | NHBenzyl | C=NH(NH₂) | 0 | — |
| 213 | | —CH₂SCH₂— | NHBenzyl | C=NH(NH₂) | 0 | — |
| 214 | | —CH₂CH₂CH₂— | NHCH₃ | H | 0 | — |
| 215 | | —CH₂CH₂CH₂CH₂— | NHCH₂CH₃ | H | 0 | — |
| 216 | | —CH₂CH₂CH₂CH₂CH₂— | NHC(CH₃)₃ | H | 0 | — |
| 217 | | —CH₂CH₂NHCH₂— | NHCH₃ | H | 0 | — |
| 218 | | —CH₂CH₂OCH₂— | NHCH₂CH₃ | H | 0 | — |
| 219 | | —CH₂SCH₂— | NHC(CH₃)₃ | H | 0 | - |
| 220 | H | H | NHBenzyl | H | 1 | NH² |
| 221 | H | CH₃ | NHBenzyl | H | 1 | NH² |
| 222 | C(CH₃)₃ | H | NHBenzyl | H | 1 | NH² |
| 223 | C(CH₃)₃ | CH₃ | NHBenzyl | H | 1 | NH² |
| 224 | H | H | NHBenzyl | C=NH(NH₂) | 1 | H |
| 225 | C=NH(NH₂) | H | NHBenzyl | H | 1 | H |
| 226 | C=NH(NH₂) | H | NHBenzyl | C=NH(NH₂) | 1 | H |

TABLE 2

Compounds of formula (I), wherein R⁶, so far as present, means hydrogen

| No. | R¹ | R² | R³ | R⁴ | n | X |
|---|---|---|---|---|---|---|
| 227 | H | H | NHBenzyl | H | 0 | NHCH(C=O)(CH₂)₃NH₂ |
| 228 | H | CH₃ | NHBenzyl | H | 0 | NHCH(C=0)(CH₂)₃NH₂ |
| 229 | H | CH₂OH | NHBenzyl | H | 0 | NHCH(C=O)(CH₂)₃NH₂ |
| 230 | H | (CH₂)₂NH₂ | NHBenzyl | H | 0 | NHCH(C=O)(CH₂)₃NH₂ |
| 231 | H | (CH₂)₃NH₂ | NHBenzyl | H | 0 | NHCH(C=O)(CH₂)₃NH₂ |
| 232 | H | CH₂NH₂ | NHBenzyl | H | 0 | NHCH(C=O)(CH₂)₃NH₂ |
| 233 | H | (CH₂)₄NH₂ | NHBenzyl | H | 0 | NHCH(C=O)(CH₂)₃NH₂ |
| 234 | H | (CH₂)₃NHC=NH(NH₂) | NHBenzyl | H | 0 | NHCH(C=O)(CH₂)₃NH₂ |
| 235 | H | CH₂CH₃ | NHBenzyl | H | 0 | NHCH(C=O)(CH₂)₃NH₂ |
| 236 | H | (CH₂)₂CH₃ | NHBenzyl | H | 0 | NHCH(C=O)(CH₂)₃NH₂ |
| 237 | H | CH(CH₃)₂ | NHBenzyl | H | 0 | NHCH(C=O)(CH₂)₃NH₂ |
| 238 | H | CH₂CH(CH₃)₂ | NHBenzyl | H | 0 | NHCH(C=O)(CH₂)₃NH₂ |
| 239 | H | CH(CH₃)CH₂—CH₃ | NHBenzyl | H | 0 | NHCH(C=O)(CH₂)₃NH₂ |
| 240 | H | (CH₂)₂SCH₃ | NHBenzyl | H | 0 | NHCH(C=O)(CH₂)₃NH₂ |
| 241 | H | CH₂COOH | NHBenzyl | H | 0 | NHCH(C=O)(CH₂)₃NH₂ |
| 242 | H | CH₂CONH₂ | NHBenzyl | H | 0 | NHCH(C=O)(CH₂)₃NH₂ |
| 243 | H | (CH₂)₂OH | NHBenzyl | H | 0 | NHCH(C=O)(CH₂)₃NH₂ |
| 244 | H | CH(CH₃)OH | NHBenzyl | H | 0 | NHCH(C=O)(CH₂)₃NH₂ |
| 245 | H | (CH₂)₂COOH | NHBenzyl | H | 0 | NHCH(C=O)(CH₂)₃NH₂ |
| 246 | H | (CH₂)₂CONH₂ | NHBenzyl | H | 0 | NHCH(C=O)(CH₂)₃NH₂ |
| 247 | H | CH₂Phenyl | NHBenzyl | H | 0 | NHCH(C=O)(CH₂)₃NH₂ |
| 248 | H | CH₂-4-OH-Phenyl | NHBenzyl | H | 0 | NHCH(C=O)(CH₂)₃NH₂ |
| 249 | H | Phenyl | NHBenzyl | H | 0 | NHCH(C=O)(CH₂)₃NH₂ |
| 250 | H | CH₂-4-Imidazolyl | NHBenzyl | H | 0 | NHCH(C=O)(CH₂)₃NH₂ |
| 251 | H | CH₂-3-Indolyl | NHBenzyl | H | 0 | NHCH(C=O)(CH₂)₃NH₂ |
| 252 | H | H | NHBenzyl | C(=NH)NH₂ | 0 | NHCH(C=O)(CH₂)₃NH₂ |
| 253 | H | CH₃ | NHBenzyl | C(=NH)NH₂ | 0 | NHCH(C=O)(CH₂)₃NH₂ |
| 254 | H | H | NHBenzyl | H | 0 | NHCH(C=O)(CH₂)₃NHC—(=NH)NH₂ |
| 255 | H | CH₃ | NHBenzyl | H | 0 | NHCH(C=O)(CH₂)₃NHC—(=NH)NH₂ |
| 256 | H | H | NHBenzyl | C(=NH)NH₂ | 0 | NHCH(C=O)(CH₂)₃NHC—(=NH)NH₂ |
| 257 | H | CH₃ | NHBenzyl | C(=NH)NH₂ | 0 | NHCH(C=O)(CH₂)₃NHC—(=NH)NH₂ |
| 258 | H | H | NHBenzyl | H | 1 | NHCH(C=O)(CH₂)₄NH₂ |
| 259 | H | CH₃ | NHBenzyl | H | 1 | NHCH(C=O)(CH₂)₄NH₂ |
| 260 | H | H | NHBenzyl | H | 2 | NHCH(C=O)(CH₂)₅NH₂ |
| 261 | H | CH₃ | NHBenzyl | H | 2 | NHCH(C=O)(CH₂)₅NH₂ |

TABLE 3

Compounds of formula (I), wherein n represents 1

| No. | R¹ | R⁶ | R² | R³ | R⁴ | X |
|---|---|---|---|---|---|---|
| 262 | H | NH₂ | H | NHBenzyl | H | NHCH(C=O)(CH₂)₄NH₂ |
| 263 | H | NH₂ | CH₃ | NHBenzyl | H | NHCH(C=O)(CH₂)₄NH₂ |

TABLE 3-continued

Compounds of formula (I), wherein n represents 1

| No. | R$^1$ R$^6$ | R$^2$ | R$^3$ | R$^4$ | X |
|---|---|---|---|---|---|
| 264 | —CH$_2$CH$_2$— | H | NHBenzyl | H | Bond |
| 265 | —CH$_2$NH— | H | NHBenzyl | H | Bond |
| 266 | —CH$_2$CH$_2$CH$_2$— | H | NHBenzyl | H | Bond |
| 267 | —CH$_2$CH$_2$NH— | H | NHBenzyl | H | Bond |
| 268 | —CH$_2$CH$_2$CH$_2$CH$_2$— | H | NHBenzyl | H | Bond |
| 269 | —CH$_2$CH$_2$— | H | NHBenzyl | C(=NH)NH$_2$ | Bond |
| 270 | —CH$_2$NH— | H | NHBenzyl | C(=NH)NH$_2$ | Bond |
| 271 | —CH$_2$CH$_2$CH$_2$— | H | NHBenzyl | C(=NH)NH$_2$ | Bond |
| 272 | —CH$_2$CH$_2$NH— | H | NHBenzyl | C(=NH)NH$_2$ | Bond |
| 273 | —CH$_2$CH$_2$CH$_2$CH$_2$— | H | NHBenzyl | C(=NH)NH$_2$ | Bond |

The compounds of formula (I) may form mono- or polyvalent, homogeneous or mixed salts with acids, e.g. with mineral acids such as hydrogen chloride, hydrogen bromide, sulphuric acid or phosphoric acid; or with appropriate carboxylic acids, e.g. aliphatic mono- or dicarboxylic acids such as formic acid, acetic acid, trifluoroacetic acid, trichloroacetic acid, propionic acid, glycolic acid, succinic acid, fumaric acid, malonic acid, maleic acid, oxalic acid, phthalic acid, citric acid, lactic acid or tartaric acid; or with aromatic carboxylic acids such as benzoic acid or salicylic acid; or with aromatic-aliphatic carboxylic acids such as mandelic acid or cinnamic acid; or with heteroaromatic carboxylic acids such as nicotinic acid; or with aliphatic or aromatic sulfonic acids such as methanesulfonic acid or toluenesulfonic acid. Dermatologically compatible salts are preferred. Salts with acetic acid and/or trifluoroacetic acid and/or lactic acid are particularly preferred.

The compounds of general formula (I) and the salts thereof may be present as optically pure isomers or as mixtures of different isomers, e.g. as racemates, and/or as mixtures of rotamers.

According to the present invention, the compounds of general formula I and the salts thereof can be manufactured according to methods known per se in peptide chemistry by completely synthesizing the compound of formula (I), possibly cleaving the remaining protective group(s), possibly alkylating a free amino group or converting it into a guanidino function and/or esterifying or amidating a free carboxyl group and/or converting an obtained basic compound into an acid addition salt and/or an obtained acid addition salt into the corresponding conjugate base or into another salt.

The compounds of formula I of the present invention and the salts thereof can be processed into topically applicable preparations according to common methods. The compounds of general formula I and their salts may be incorporated in the topically applicable end product in concentrations ranging from 0.5 to 5,000 ppm (w/w), preferably from 1 to 1000 ppm (w/w), calculated on the weight of the compound of the present invention or of one of their salts and of the carrier(s).

The compounds of formula I of the present invention and the salts thereof can be used in the form of a solution, a dispersion, an emulsion or encapsulated in carriers, such as macro-, micro- or nanocapsules, in liposomes or chylomicrons, or enclosed in macro-, micro- or nanoparticles or in microsponges or absorbed on powdered organic polymers, talc, bentonite and other mineral carriers.

The compounds of formula I of the present invention and the salts thereof can be used in each form appropriate for topically applicable preparations, such as O/W and W/O emulsions, milk, lotions, ointments, gel-forming and viscous, surfactant and emulsifying polymers, pomades, shampoos, soaps, gels, powders, sticks and pencils, sprays, body oils, face masks and plasters.

The compounds of formula I of the present invention and the salts thereof can be used together with any other commonly used ingredient of topically applicable preparations, such as extraction lipids and/or synthetic lipids, gel-forming and viscous, surfactant and emulsifying polymers, water- or fat-soluble actives, plant extracts, tissue extracts, sea extracts, sunscreens, antioxidants, moisturizers and barrier substances as well as skin-revitalizing actives.

The compounds of the present invention can be used together with any other commonly used, topically applicable skin care active. Additional skin care actives may be for example anti-wrinkle actives/anti-atrophy actives: the compositions of the present invention may contain a safe and effective quantity of one or several anti-wrinkle actives or anti-atrophy actives. Anti-wrinkle/anti-atrophy actives which are appropriate for incorporation in the compositions of the present invention comprise sulphur-containing D- and L-aminoacids and their derivatives and salts, in particular the N-acetyl derivatives, whereby a preferred example thereof is N-acetyl-L-cysteine; thiols, e.g. ethanethiol; hydroxy acids, phytic acid, liponic acid, lysophosphatidinic acid; skin-peeling substances (e.g. phenol and similar); vitamin B3 compounds and retinoids which improve the wrinkle-smoothing properties of the compounds of formula I of the present invention and the salts thereof.

Three classes of such commonly used, topically applicable skin care substances are discussed more closely hereinafter, namely vitamin B3 compounds, retinoids and hydroxy acids.

a) Vitamin B3 Compounds:

The compositions of the present invention can contain a safe and effective quantity of a vitamin B3 compound. Vitamin B3 compounds are particularly useful to regulate the skin's state as described in WO 97/39733 A1 (published on Oct. 30, 1997). Examples of derivatives of the cited vitamin B3 compounds comprise nicotinates including non-vasodilating esters of nicotinic acid (e.g. tocopheryl nicotinate), nicotinyl amino acids, nicotinyl alcohol esters of carboxylic acids, nicotinic acid-N-oxide and niacinamide-N-oxide.

b) Retinoids:

The compositions of the present invention may also contain a retinoid. "Retinoids" in this case comprise all natural and/or synthetic analogues of vitamin A or retinol-like compounds which possess the biological efficacy of vitamin A in skin as well as the geometrical isomers and stereoisomers of these compounds. The retinoid is preferably retinol, a retinol ester (e.g. C$_2$ to C$_{22}$ alkylester of retinol, including retinyl palmitate, retinyl acetate and retinyl propionate), retinal and/or retinic acid (including all-trans retinic acid and/or 13-cis retinic acid), in particular a retinoid different from retinic acid. Other appropriate retinoids are tocopheryl retinoate [tocopherol ester of retinic acid (trans or cis)], adaptalen {6-[3-(1-adamantyl)-4-methoxyphenyl]-2-naphthoic acid} and tazaroten (ethyl-6-[2-(4,4-dimethylthiochroman-6-yl)-ethinyl]nicotinate). Preferred retinoids are retinol, retinyl palmitate, retinyl acetate, retinyl propionate, retinal and combinations thereof. The compositions of the present invention may contain a safe and efficient quantity of retinoid, so that the resulting composition is safe and efficient for regulating the state of the horny skin, preferably for regulating visible and/or sensible skin discontinuities, in particular for regulating skin aging signs, very particularly for regulating age-related visible and/or sensible discontinuities in the skin smoothness.

(c) Hydroxy Acids:

The compositions of the present invention may contain a safe and efficient quantity of hydroxy acid. Preferred hydroxy acids to use in the compositions of the present invention comprise α-hydroxy acids, such as lactic acid and glycolic acid, or α-hydroxy acids such as salicylic acid and salicylic acid derivatives, e.g. its octanoyl derivative.

Moreover, additional peptides including, but not exclusively, di-, tri-, tetra-, penta- and hexapeptides and their derivatives may be added to the compositions of the present invention in safe and efficient quantities. In this case, "peptides" relates to naturally occurring peptides as well as synthetic peptides and also comprises peptidomimetics and metal complexes of "peptides". Naturally occurring and commercially available compositions that contain peptides can also be used.

Dipeptides appropriate for use in the preparations of the present invention include carnosine (β-Ala-His) and appropriate tripeptides comprise Gly-His-Lys, Arg-Lys-Arg and His-Gly-Gly. Preferred tripeptides and derivatives thereof include palmitoyl-Gly-His-Lys, that can be purchased as Biopeptide CL™ (100 ppm palmitoyl-Gly-His-Lys, commercially available from Sederma, France), peptide CK (Arg-Lys-Arg), peptide CK+ (Ac-Arg-Lys-Arg-NH$_2$) and a copper complex of Gly-His-Lys or His-Gly-Gly that can be obtained as lamine from Sigma (St. Louis, Mo., USA). Tetrapeptides appropriate for use in the preparations of the present invention comprise peptide E, Arg-Ser-Arg-Lys. Examples of pentapeptides are matrixyl (palmitoyl-Lys-Thr-Thr-Lys-Ser), available from Sederma, France, and those described in WO 03/037933. An hexapeptide appropriate for use in the compositions of the present invention is argireline (Ac-Glu-Glu-Met-Gln-Arg-Arg-NH$_2$), manufactured by Lipotec, Spain.

The compounds of the present invention as well as the topically applicable compositions containing same are incorporated in skin care products, in particular for the treatment of mimic and age-related wrinkles.

The following examples should explain the invention without limiting its scope. Used abbreviations are:

| | |
|---|---|
| NMR | Nuclear magnetic resonance |
| MS | Mass spectrometry |
| Fmoc | 9-Fluorenylmethyloxycarbonyl |
| Boc | tert.-Butyloxycarbonyl |
| Z | Benzyloxycarbonyl |
| Dab | 2,4-Diaminobutyric acid |
| Dap | 2,3-Diaminopropionic acid |
| Gab | 2-Amino-4-guanidino-butyric acid |
| Pro | Proline [(−)-pyrrolidin-2-carboxylic acid] |
| β-Ala | β-Alanine (3-aminopropionic acid) |
| EtOAc | Ethylacetate |
| DCM | Dichloromethane |
| DMF | Dimethylformamide |
| TBTU | O-(Benzotriazol-1-yl)-N,N,N',N'-tetramethyluronium tetrafluoroborate |
| DIPEA | Diisopropylethylamine |
| NMM | N-Methylmorpholine |
| HOBt | 1-Hydroxybenzotriazol |
| DCC | N,N'-Dicyclohexylcarbodiimide |
| TFA | Trifluoroacetic acid |
| GF/A | Glass fibre microfilter |
| ACN | Acetonitrile |
| RT | Room temperature |
| HPLC | High pressure liquid chromatography |
| THF | Tetrahydrofuran |
| MEM | Minimum essential medium |
| M199 | Medium 199 (TECOmedical Ltd.) |
| Bzl | Benzyl |

EXAMPLE 1

Manufacture of the Compounds of the Present Invention

The following embodiment 1.1 describes the manufacture of a representative of the compounds of formula (I) of the present invention and of salts of such compounds. Analysis of the eluates and products obtained according to the examples was performed by proton NMR spectroscopy, HPLC electrospray MS or microanalysis. The compounds can be manufactured according to the known methods described hereinafter (general instructions of M. Bodanszky "The Practice of Peptide Synthesis" Springer, $2^{nd}$ Edition 1994). The P1 amino acid at the carboxy terminus is correspondingly derivatized, the α-amino protective group (e.g. a Boc group) is eliminated and the peptide is built step-wise using the usual reagents in peptide synthesis until completion of the desired sequence, whereupon the side chain protective groups (e.g. Z or Boc functions) are split off.

1.1 Compound No. 4.5 (see Table 4, below)

1.1.1 Boc-Dab(Z)-NHBzl 1.4 g of Boc-Dab(Z)-OH was dissolved in 10 ml of ACN and 5 ml of DMF, 1.35 g of TBTU and 1.43 ml of DIPEA were added, whereupon 0.88 ml of benzylamine was added and the mixture was stirred for 1 h at RT. The solvent was evaporated, the residue was taken in EtOAc and the solution was washed 3× with Na$_2$CO$_3$ 10%, citric acid 10% and saturated NaCl solution. After drying over Na$_2$SO$_4$, evaporation of the solvent and vacuum-drying at 40° C. overnight, 1.8 g of oily product was isolated.

1.1.2 H-Dab(Z)-NHBzl.TFA 1.8 g of compound 1.1.1 was dissolved in 15 ml of DCM, 5 ml of TFA were added and the solution was stirred for 30 min at RT. After evaporation of the solvent, the crude product was purified by preparative HPLC and 0.60 g of the desired compound was isolated. The theoretical mass of 342 was confirmed by a result of 342.

1.1.3 Boc-Pro-Dab(Z)-NHBzl 0.42 g of Boc-Pro-OH was dissolved in 8 ml of THF and 16 ml of ACN, 0.63 g of TBTU and 0.66 ml of DIPEA were added and the mixture was stirred at RT. After 3 min a solution composed of 0.60 g of compound 1.1.2 and 0.143 ml of NMM in 10 ml of THF and 2 ml of DMF were added. After stirring for 1 h at RT, the solvents were evaporated and the residue was taken in EtOAc and washed 3× with Na$_2$CO$_3$ solution 10%, citric acid 10% and saturated NaCl solution. After drying over Na$_2$SO$_4$, evaporation of the solvent and vacuum-drying at 40° C. overnight, 0.8 g of oily crude product was isolated.

1.1.4 H-Pro-Dab(Z)-NHBzl.HCl 0.8 g of the above compound 1.1.3 was dissolved in 6 ml of a 4M HCl solution in dioxan and stirred for 1 h at RT. After evaporation of the solvent, the crude product was chromatographed by preparative HPLC, whereby 0.6 g of the desired compound was obtained. The theoretical mass of 439 was confirmed by a result of 439.

1.1.5 Z-β-Ala-Pro-Dab(Z)-NHBzl 0.34 g of Z-β-Ala-OH was dissolved in 10 ml of THF and cooled in an ice bath to 5° C., whereupon 0.17 g of HOBt and 0.31 g of DCC were added. After 45 min a solution composed of 0.6 g of compound 1.1.4 in 10 ml of THF and 0.14 ml of NMM was added. After stirring at RT for 18 h the formed, precipitated urea derivative was filtered off, the solvent was evaporated and the residue was taken in EtOAc and washed 3× with $Na_2CO_3$ solution 10%, citric acid 10% and saturated NaCl solution. After drying over $Na_2SO_4$ and evaporation of the solvent, the crude product was chromatographed by preparative HPLC. 0.5 g of a colourless oil of the desired compound was isolated. The theoretical mass of 644 was confirmed by a result of 644.

1.1.6 H-β-Ala-Pro-Dab-NHBzl.2TFA 0.5 g of compound 1.1.5 was dissolved in 20 ml of acetic acid and 1 ml of TFA and the solution was mixed with a suspension of 100 mg of palladium on carbon 10% in 5 ml of water. Hydrogen gas was applied until saturation and hydration occurred at normal pressure until complete conversion (approx. 12 h). The suspension was filtered through a GF/A filter and the solvent was evaporated. The obtained crude product was purified by preparative HPLC and, after evaporation of the solvent, dissolved in water and lyophilized. 0.34 g of the desired compound was obtained. The theoretical mass of 376 was confirmed by a result of 376.

The other compounds of Table 4 can be prepared analogously.

TABLE 4

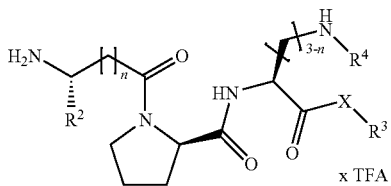

x TFA

| No. | $R^2$ | $R^3$ | $R^4$ | n | X | MS data |
|---|---|---|---|---|---|---|
| 4.1 | H | NH-Benzyl | C(=NH)NH$_2$ | 0 | Bond | 418 |
| 4.2 | CH$_3$ | NH-Benzyl | C(=NH)NH$_2$ | 0 | Bond | 432 |
| 4.3 | CH$_3$ | NH-Benzyl | C(=NH)NH$_2$ | 0 | NHCH(C=O)(CH$_2$)$_3$NH—C(=NH)NH$_2$ | 588 |
| 4.4 | CH$_3$ | NH-Benzyl | H | 0 | Bond | 390 |
| 4.5 | H | NH-Benzyl | H | 1 | Bond | 376 |
| 4.6 | CH$_2$NH$_2$ | NH-Benzyl | C(=NH)NH$_2$ | 0 | Bond | 447 |
| 4.7 | CH$_3$ | NH-(CH$_2$)$_2$-Phenyl | C(=NH)NH$_2$ | 0 | Bond | 446 |
| 4.8 | CH$_3$ | NH-(4-CH$_3$O-Benzyl) | C(=NH)NH$_2$ | 0 | Bond | 462 |
| 4.9 | H | NHBenzyl | H | 1 | NHCH(C=O)(CH$_2$)$_4$NH$_2$ | |
| 4.10 | H | NHBenzyl | C(=NH)NH$_2$ | 1 | Bond | |

4.11

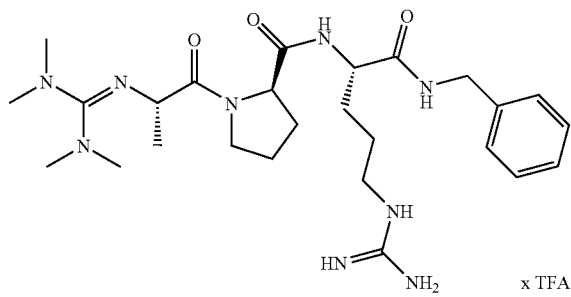

530 x TFA 4.12

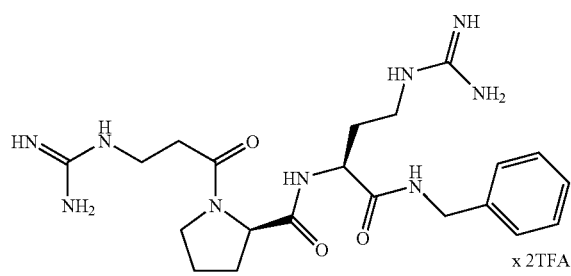

x 2TFA

TABLE 4-continued

| No. | R² | R³ | R⁴ | n | X | MS data |
|-----|----|----|----|----|----|---------|
| 4.13 | (structure: piperidin-3-yl group) | (NH₂, homo-side chain) | (benzyl amide) | | x 2TFA | |
| 4.14 | (structure: piperazin-2-yl group) | (NH₂, homo-side chain) | (benzyl amide) | | x 3TFA | |
| 4.15 | (structure: 2,3-diaminopropanoyl) | (NH₂, homo-side chain) | (benzyl amide) | | x 3TFA | |

EXAMPLE 2

Efficacy Test 2.1 Material
  Normal human muscle cells (myoblasts) in the 3rd passage
  Spinal explants of a 13 day-old rat embryo with dorsal root ganglia
  Culture medium: ⅔ MEM and ⅓ M199, 2 mM L-glutamine, penicillin 50 IU/ml, streptomycin 50 µg/ml, foetal calf serum 5%
  Culture conditions: 37° C., 5% $CO_2$ 2.2 Test Description In order to test the efficacy of the compounds of the present invention, a co-culture model of human muscle cells on one hand and neurons from the spinal marrow of rat embryos on the other hand was established.

Normal human muscle cells (myoblasts) were cultured in gelatine-coated 24-well plates until a monolayer of myofibrils (from fused muscle cells) had formed. Afterwards, an explant of the spinal marrow of a 13 day-old rat embryo with dorsal root ganglia was placed on the muscle cell monolayer. After one day of co-culture, the first axons were seen to grow out of the explant to come in contact with muscle cells. The first contractions appeared after 5 days. After three weeks of co-culture, a well differentiated model of striped muscle fibres with fully developed neuromuscular junctions, comparable to a motor end plate, was formed (junction of nerve and muscle). At this stage of development, the myofibrils performed regular contractions and the model was used for the tests.

The frequency of contractions was observed for 30 sec by means of an inverted microscope connected to a video recorder, whereupon the compounds to test, pre-diluted in culture medium, were added in the corresponding concentrations. The contractions were counted again for 30 sec and namely 1 min and 2 h after addition of the substances. After an incubation period of 48 h and a visual control of the co-culture, the contractions were counted again before and after addition of glucose (end concentration 1 g/liter) to also exclude an effect due to the lack of glucose.

2.3 Results (see Table 5)

TABLE 5

Variation Δ [in %] of the number of muscle contractions (measured for 30 seconds) 1 minute, 2 hours and 48 hours after incubation of the product in comparison to the number of contractions before incubation of the product (means of 3 measurements)

| Product No. | Concentration | Δ [%] (1 min) | Δ [%] (2 h) | Δ [%] (48 h) |
|-------------|---------------|---------------|-------------|--------------|
| Control | — | 92 | 105 | 108 |
| 4.2 | 1.0 mM | 85 | 12 | 60 |
|  | 0.5 mM | 93 | 37 | 36 |
|  | 0.1 mM | 85 | 78 | 37 |

TABLE 5-continued

Variation Δ [in %] of the number of muscle contractions (measured for 30 seconds) 1 minute, 2 hours and 48 hours after incubation of the product in comparison to the number of contractions before incubation of the product (means of 3 measurements)

| Product No. | Concentration | Δ [%] (1 min) | Δ [%] (2 h) | Δ [%] (48 h) |
|---|---|---|---|---|
| 4.3 | 1.0 mM | 25 | 0 | 7 |
|  | 0.5 mM | 73 | 1 | 87 |
|  | 0.1 mM | 91 | 5 | 88 |
| 4.5 | 1.0 mM | 24 | 0 | 0 |
|  | 0.5 mM | 96 | 0 | 0 |
|  | 0.1 mM | 86 | 4 | 4 |
| 4.6 | 1.0 mM | 68 | 35 | 0 |
|  | 0.5 mM | 78 | 42 | 0 |
|  | 0.1 mM | 85 | 68 | 43 |
| 4.7 | 1.0 mM | 105 | 65 | 3 |
|  | 0.5 mM | 91 | 0 | 34 |
|  | 0.1 mM | 103 | 69 | 74 |
| 4.8 | 1.0 mM | 100 | 58 | 32 |
|  | 0.5 mM | 84 | 90 | 78 |
|  | 0.1 mM | 85 | 37 | 132 |
| 4.11 | 1.0 mM | 104 | 7 | 0 |
|  | 0.5 mM | 105 | 16 | 22 |
|  | 0.1 mM | 105 | 75 | 96 |
| Product A (comparison) | 1.0 mM | 99 | 88 | n.d. |
|  | 0.5 mM | 106 | 91 | n.d. |
|  | 0.1 mM | 103 | 120 | n.d. |
|  | 0.05 mM | 103 | 96 | n.d. | n.d. = not determined

EXAMPLE 3

Formulation of an Ointment (Containing the Ingredients Mentioned in the Following Table 6)

Method: The ingredients 1-5 (A) are heated to 70° C. The ingredients 6-7 (B) are heated to 75° C. B is added to A under stirring, cooled to 50° C., homogenized and cooled to 30° C. Afterwards, the ingredients 8-9 (C) and ingredient 10 (D) are added one after the other and stirred cold.

TABLE 6

| No. | Ingredient | % w/w |
|---|---|---|
| 1 | (A) Tego Care 450 | 3.00 |
| 2 | Cetearylalcohol | 2.25 |
| 3 | Glycerylstearate | 2.25 |
| 4 | Cetiol 868 | 10.00 |
| 5 | Squalane | 5.00 |
| 6 | (B) Deionized water | 66.99 |
| 7 | Sodium hyaluronate | 5.00 |
| 8 | (C) Glycerin | 5.00 |
| 9 | Phenonip | 0.50 |
| 10 | (D) Compound No. 4.5 (Tab. 4) | 0.01 |

EXAMPLE 4

Formulation of a Gel (Containing the Ingredients Mentioned in the Following Table 7)

Method: The ingredients 2-6 are successively diluted in deionized water (1) (A). The pH is adjusted to 6.0 with ingredient 7 (B), whereupon ingredient 8 (C) is added.

TABLE 7

| No. | Ingredient | % w/w |
|---|---|---|
| 1 | (A) Deionized water | 92.09 |
| 2 | 1,3-Butanediol | 5.00 |
| 3 | Phenonip | 0.50 |
| 4 | Abil B 8843 | 1.50 |
| 5 | Carboxymethyl Cellulose | 0.15 |
| 6 | Carbopol Ultrez 10 | 0.75 |
| 7 | (B) NaOH |  |
| 8 | (C) Compound No 4.7 (Tab. 4) | 0.01 |

The invention claimed is:
1. Compounds of general formula (I)

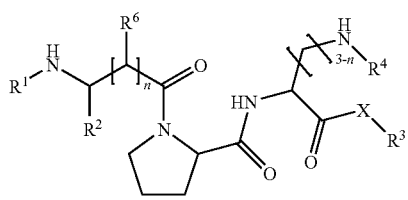

wherein
X represents a bond or NH—CH(C═O)—(CH$_2$)$_{3+n}$NH—R$^5$,
n represents 0, 1 or 2,
R$^1$, R$^4$ and R$^5$—independently from each other—represent hydrogen, optionally substituted C$_1$-C$_6$-alkyl, amindino or tetra-C$_1$-C$_6$-alkylamidinium,
R$^2$ represents hydrogen, or C$_1$-C$_6$-alkyl, or hydroxy-, amino-, guanidino-, methylthio-, carboxyl- or carbamoyl-substituted C$_1$-C$_6$-alkyl, or substituted heteroaryl-substituted C$_1$-C$_6$-alkyl,
or
R$^1$ and R$^2$ together with the residue to which they are bound represent a 5- to 7-membered, saturated ring,
R$^3$ represents optionally substituted aryl-C$_1$-C$_6$-alkylamino, and
R$^6$ represents hydrogen or, when n is 1, also amino or together with R$^1$ and the residue to which R$^6$ and R$^1$ are bound a 5- to 7-membered, saturated ring.

2. Compounds according to claim 1, wherein R$^1$ means hydrogen.

3. Compounds according to claim 1, wherein R$^2$ means hydrogen or methyl.

4. Compounds according to claim 1, wherein R$^3$ means aryl-C$_1$-C$_6$-alkylamino.

5. Compounds according to claim 1, wherein n means 0 or 1.

6. Compounds according to claim 1, wherein R$^1$ means hydrogen, R$^2$ means hydrogen or methyl, and n means 0 or 1.

7. Compounds according to claim 1, wherein the compounds of formula (I) are present as mono- or polyvalent, homogeneous or mixed salts with acids.

8. Compounds according to claim 7, wherein they are present as salts with inorganic and/or organic acids.

9. Compounds according to claim 8, wherein they are present as salts with aliphatic, saturated and/or unsaturated mono- and/or dicarboxylic acids, and/or with aromatic carboxylic acids, and/or with aromatic-aliphatic carboxylic acids, and/or with heteroaromatic carboxylic acids, and/or with aliphatic and/or aromatic sulfonic acids.

10. Compounds according to claim 7, wherein they are present as salts with hydrogen chloride and/or hydrogen bromide and/or sulphuric acid and/or phosphoric acid and/or formic acid and/or acetic acid and/or trifluoroacetic acid and/or trichloroacetic acid and/or propionic acid and/or maleic acid and/or oxalic acid and/or phthalic acid and/or citric acid and/or lactic acid and/or tartaric acid and/or benzoic acid and/or salicylic acid and/or mandelic acid and/or cinnamic acid and/or nicotinic acid and/or methanesulfonic acid and/or toluenesulfonic acid.

11. Compounds according to claim 10, wherein they are present as salts with acetic acid and/or trifluoroacetic acid and/or lactic acid.

12. Compounds according to claim 1, wherein they are present as optically pure isomers or as mixtures of different isomers and/or as mixtures of rotamers.

13. H-Ala-Pro-Arg-Arg-NH-benzyl.

14. H-(β-Ala)-Pro-Dab-NH-benzyl.

15. H-Dap-Pro-Arg-NH-benzyl.

16. H-Ala-Pro-Arg-NH-$(CH_2)_2$-phenyl.

17. H-(β-Ala)-Pro-Gab-NH-benzyl.

18. N-[bis(dimethylamino)methylen]-Ala-Pro-Arg-NH-benzyl.

19. Acid addition salts of the compound according to claim 13.

20. A method for preparing the compounds according to claim 1, which, by using methods known per se in peptide chemistry, comprises completely synthesizing the compound of formula (I), optionally cleaving the remaining protective group(s), optionally alkylating a free amino group or converting it into a guanindino function and/or esterifying or amidating a free carboxyl group and/or converting an obtained basic compound into an acid addition salt and/or an obtained acid addition salt into the corresponding conjugate base or into another salt.

21. The method for preparing as topically applicable actives or for the preparation of topically applicable compositions, respectively, employing a compound of claim 1.

22. The method according to claim 21, wherein the compounds are applied for skin care or for the preparation of skin care products, respectively.

23. The method according to claim 22, wherein the compounds or the skin care products, respectively, are applied for the treatment of mimic and/or age-related wrinkles in human skin.

24. A topically applicable composition wherein it contains at least one compound according to claim 1.

25. A topically applicable composition where it contains at least one compound according to claim 1 in a quantity ranging between 0.5 ppm and 5,000 ppm (w/w), calculated on the weight of the compound(s) and of the carrier(s).

26. A topically applicable composition wherein it contains at least one compound according to claim 1 in a quantity ranging between 1 ppm and 1000 ppm (w/w), calculated on the weight of the compound(s) and of the carrier(s).

27. A composition according to claim 24 as a topically applicable skin care product.

28. A composition according to claim 27 for the treatment of mimic and/or age-related wrinkles in human skin.

29. A composition according to claim 24, wherein it contains further ingredients commonly used in topically applicable compositions which are selected from the group comprising extraction lipids and/or synthetic lipids, gel-forming and viscous, surfactant and emulsifying polymers, water- or fat-soluble actives, plant extracts, tissue extracts, sea extracts, synthetic products, sun protection products, antioxidants, moisturizers and barrier substances and/or skin-revitalizing actives.

30. A topically applicable composition wherein it contains
a) at least one compound according to claim 1 and
b) a safe and efficient quantity of at least one additional skin care active selected among the anti-wrinkle or anti-atrophy actives.

31. A composition according to claim 24, wherein it may be in the form of a solution, a dispersion, an emulsion, a milk, a lotion or an ointment, a gel-forming and viscous, surfactant and emulsifying polymer, a pomade, a shampoo, a soap, a gel, a powder, a stick, a pencil, a spray or a body oil or encapsulated in carriers.

32. A composition according to claim 31, wherein it may be encapsulated in macro-, micro- or nanocapsules, in liposomes or chylomicrons, or enclosed in macro-, micro- or nanoparticles or in microsponges, or absorbed on powdered organic polymers, talk, bentonite and/or other miner carriers.

33. A method for the treatment of mimic and/or age-related wrinkles in human skin, comprising the application of a compound according to claim 1 or of a composition containing said compound on the skin.

34. A method according to claim 33, wherein it is applied as a cosmetic treatment.

* * * * *